United States Patent
Arnold et al.

[11] Patent Number: 5,955,840
[45] Date of Patent: *Sep. 21, 1999

[54] METHOD AND APPARATUS TO GENERATE ULTRAVIOLET (UV) RADIATION, SPECIFICALLY FOR IRRADIATION OF THE HUMAN BODY

[75] Inventors: Erich Arnold, Mainz; Friedel Maul, Erlensee; Alexander Dohn, Limeshain-Hainchen, all of Germany

[73] Assignee: Heraeus Noblelight GmbH, Hanau, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/748,593

[22] Filed: Nov. 13, 1996

[30] Foreign Application Priority Data

Nov. 22, 1995 [DE] Germany ............... 195 43 342

[51] Int. Cl.$^6$ ............... H01J 17/20; H01J 61/12; H01J 11/00; H01J 65/00
[52] U.S. Cl. ............... 313/637; 313/234; 313/607; 313/631; 313/634; 313/492; 313/493; 128/303.1
[58] Field of Search ............... 313/493, 607, 313/234, 631, 633–34, 491–492, 231.71, 573–76, 637, 643, 40; 128/303.1

[56] References Cited

U.S. PATENT DOCUMENTS

| | | | |
|---|---|---|---|
| 4,686,979 | 8/1987 | Gruen et al. | 128/303.1 |
| 4,837,484 | 6/1989 | Eliasson et al. | 313/607 X |
| 5,173,638 | 12/1992 | Eliasson et al. | 313/607 X |
| 5,432,398 | 7/1995 | Kogelschatz . | |
| 5,444,331 | 8/1995 | Matsuno et al. | 313/607 X |
| 5,581,152 | 12/1996 | Matsuno et al. | 313/586 X |
| 5,604,410 | 2/1997 | Vollkommer et al. | 313/607 X |
| 5,666,026 | 9/1997 | Matsuno et al. | 313/234 X |

FOREIGN PATENT DOCUMENTS

| | | |
|---|---|---|
| 0 254 111 A1 | 1/1988 | European Pat. Off. . |
| 0 254 111 B1 | 1/1988 | European Pat. Off. . |
| 0 521 553 A2 | 1/1993 | European Pat. Off. . |
| 43 24 007 A1 | 1/1995 | Germany . |

*Primary Examiner*—Sandra O'Shea
*Assistant Examiner*—Mack Haynes
*Attorney, Agent, or Firm*—Frishauf, Holtz, Goodman, Langer & Chick, P.C.

[57] ABSTRACT

A method and an apparatus for phototherapy or tanning of the human body utilizes energy most efficiently by generating incoherent excimer radiation in the wavelength bands of between 300 and 310 nm, preferably about 308 nm, and from 315 to 350 nm. A discharge space (4) is defined by a discharge vessel (3) of radiation transmissive dielectric material. A first electrode (5), preferably a mesh or a net jacket, surrounds the wall of the discharge vessel; a second electrode (7) covered by a second dielectric (8) is coaxially located within the discharge vessel. A fill of xenon halide, preferably xenon chloride with a cold-fill pressure of about 500 to 1,500 mbar is located within a discharge space (4). A voltage source (15) is connected to said first and second electrodes. The first electrode (5) can be sub-divided into electrode segments (5', 5"), for selective irradiation of portions of a body, with a switch (14), selectively connecting the segments forming the first electrode, or some, or all the segments to the voltage source. Suitably setting the cold-fill pressure can change the wavelength of the emitted excimer radiation.

14 Claims, 1 Drawing Sheet

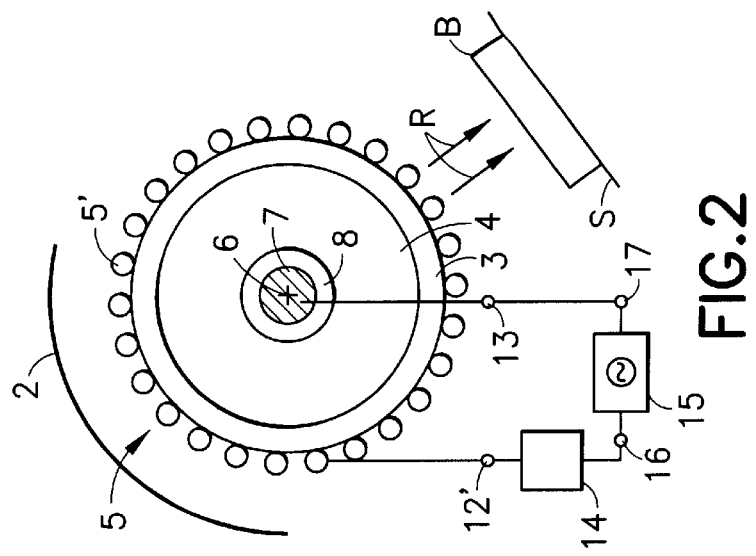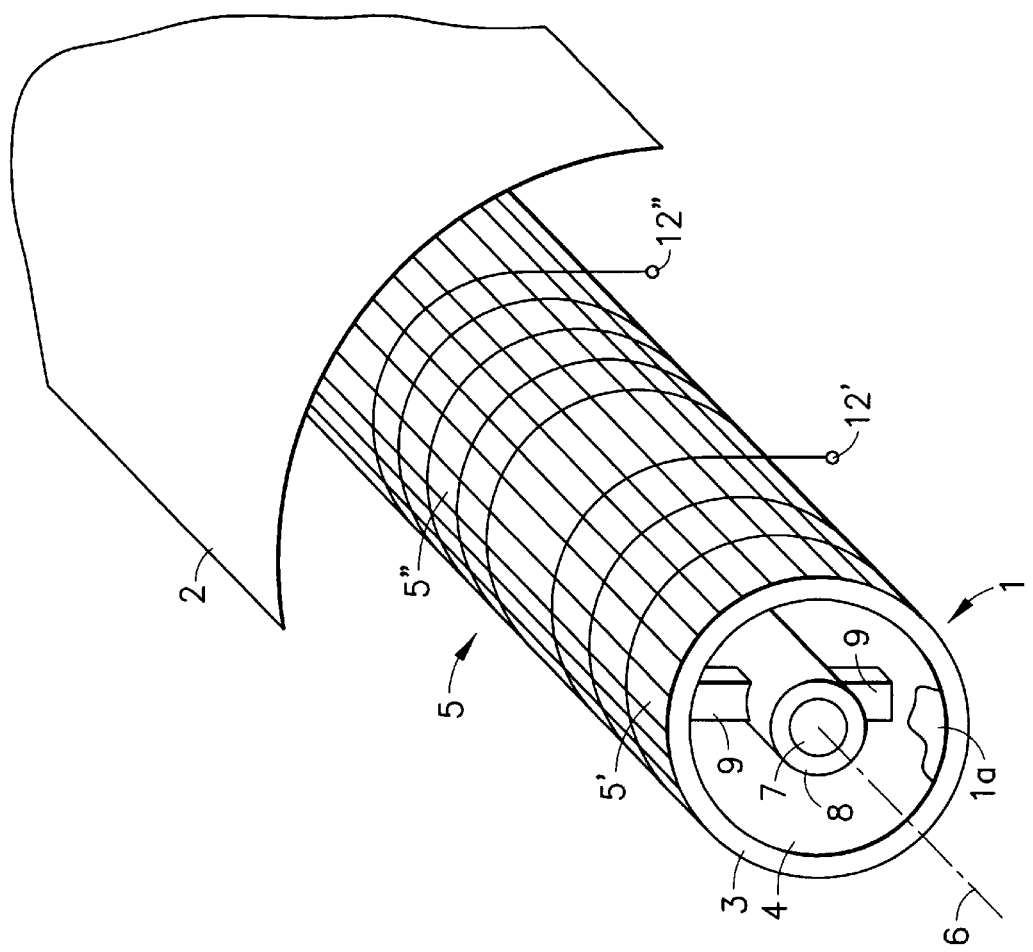

METHOD AND APPARATUS TO GENERATE ULTRAVIOLET (UV) RADIATION, SPECIFICALLY FOR IRRADIATION OF THE HUMAN BODY

REFERENCE TO RELATED PUBLICATIONS

German DE 43 24 007 A1, Brück; European 0 254 111 B1, Eliasson et al.

FIELD OF THE INVENTION

The present invention relates to generation of ultraviolet (UV) radiation, specifically for irradiation of the human body, and more particularly to irradiating the human body with the irradiation formed as an incoherent excimer radiation in the wavelength range of between about 300 to 350 nm.

BACKGROUND

German Patent Publication 43 200 007, Brück, describes a process for radiating emissions which is mild on the skin, using a light source as a component in a tanning system. The light source does not emit, or hardly emits, portions of long wave UV-A radiation. The light source is used in combination with a filter. The light source itself is a non-doped mercury high-pressure discharge lamp. Due to the absorption of radiation in the filter, a portion of the radiant energy is lost in the form of heat. The radiator-filter combination itself may be subject to high temperatures.

European Patent 0 254 111 B1, Eliasson et al., describes a UV radiator which has a discharge space, in which a fill gas is included. The discharge space is delimited by walls. At least one of the walls forms a dielectric. Two electrodes are used; at least a first electrode is located on the surface of the discharge which is remote from the dielectric; this first electrode is linear in form, e.g. a metal strip. The first electrode, as well as the dielectric, are transparent to radiation generated by a quiet electrical discharge. The second electrode has a UV radiation reflecting layer, preferably an aluminum layer. The fill gas is a noble gas, or a noble gas mixture which, under discharge conditions, generates excimers. The fill gas additionally contains mercury, nitrogen selenides, deuterium, or a mixture of these substances, alone, or in combination with a noble gas. The comparatively short wave radiation of the noble gas helium, neon, argon, xenon is, under formation of excimers, in the region of from 60 to 190 nm. This extremely short wave UV range of the spectrum is not suitable for irradiation of the human body, or for tanning. The disclosure also describes a mixture of the fill of xenon and chlorine, which emits radiation in the region of from between 300 to 320 nm, that is, a range suitable for irradiation of the human body.

European Patent 0 254 111, Eliasson et al, provides a good disclosure of radiation in the formation of excimers, and also defines excimers: an excimer is a molecule which is formed by one excited atom and one atom in base state. Upon dissociation of the excimer molecule into its constituents, the binding energy is emitted in form of UV radiation. "Excimer" is a coined word derived from excited dimer; a "dimer" is a diatomic molecule consisting of identical atoms, and excimers are excited diatomic molecules.

Transfer of electron energy into UV radiation is highly efficient with such excimers. Up to 50% of the electron energy can be changed into UV radiation. The excited complexes have a lifetime of only a few nanoseconds, or even less, e.g. tenths of a nanosecond. The wavelength of the emitted radiation is dependent on the gas which forms the excimers; for example, for helium, it is between 60 and 100 nm; for xenon, between 160 and 190 nm.

THE INVENTION

It is an object to provide a method and an apparatus or system which provides for intensive irradiation of the human body in the UV-A/UV-B region. The irradiation of the human body should be essentially monochromatic and erythemically active, for long time pigmentation, to obtain a specifically targeted phototherapy or tanning of high intensity without disadvantageous overstressing of the skin.

Briefly, the radiation is generated in form of non-coherent excimer radiation in the wavelengths within the band of 300 to 315 nm, or, respectively, in the band of from 315 to 350 nm. The apparatus to generate this radiation utilizes a discharge vessel having a confining wall of dielectric material; a first electrode is located on the wall of the discharge vessel on a surface thereof, remote from the interior of the vessel, the first electrode and the wall of the discharge vessel being radiation transmissive. A second electrode, directly or indirectly de-limiting a discharge space within the vessel, is provided. A fill of xenon halide having a cold-fill pressure of about from 500 to 1,500 mbar is located within the discharge space. A voltage source is connected to the first and second electrodes and exciting the apparatus to emit incoherent excimer radiation.

The method and the apparatus have the specific advantage that no combination of filters and radiation sources are needed, so that all energy of the excimer radiation which is available be effectively utilized. It is, hence, also possible to suitably control the emitted radiation, to satisfy a multiplicity of uses and applications. In the bandwidth of from 300 to 315 nm, the preferred wavelength of radiation is about 308 nm.

The radiation apparatus or system can be easily matched to the particular task to be accomplished, as well as to the geometry of the body, or the portion of the body to be irradiated. For example, the radiation source can be constructed in elongated form for irradiating the entire body of a patient; however, by selectively connecting, or disconnecting portions of the electrodes, the same apparatus can be controlled to irradiate particular portions of the body, as desired. It is another advantage that no delays of ignition or firing of the discharge vessel need occur, for example by suitable setting of a certain duty ratio, that is, pulse duration with respect to pulse pauses, and the irradiation obtained can be optimally matched to the particular application or use. The radiating apparatus has a high lifetime of well over 1,000 hours, which is a specific economic advantage.

In accordance with a preferred embodiment, the radiating source is constructed in coaxial form, so that radiators having a substantially smaller outer diameter than prior art radiators can be used. By segmenting the outer, first electrode, the radiation field can be matched to the particular requirements of the body part or portion to be irradiated. This is particularly advantageous when the radiation source is used for tanning.

Specifically targeted adjustment of the radiation of UV-A with respect to UV-B provides a replacement for the previously used mercury vapor low-pressure radiators, which have a short lifetime.

DRAWINGS

FIG. 1 is a highly schematic perspective view, partly broken away, of a radiation apparatus; and FIG. 2 is a highly schematic cross-section across the radiator of FIG. 1, and illustrating a body to be irradiated in schematic block form.

DETAILED DESCRIPTION

The radiating apparatus—see FIG. 1—is, essentially, an excimer radiator 1 located within a reflector arrangement 2. Both the radiator, as well as the reflector, are shown only partially, in broken-away form. The excimer radiator 1 has a hollow cylindrical dielectric vessel or body 3, the wall of which surrounds a discharge space 4. The dielectric 3 is transparent to the radiation generated within the radiation space 4. A first electrode 5, of generally mesh or net form, is located on the outer surface of the dielectric body 3. The electrode 5, due to its mesh or net-like structure is also transparent for radiation generated within the discharge space 4.

A second electrode 7 is located in the interior of the dielectric body 3, coaxial with a cylinder axis 6 of the cylindrical dielectric body 3. The electrode 7 is rod, or pinlike, and surrounded by a second dielectric 8. Support elements 9 secure the dielectric 8 within the dielectric 3; the electrode 7 is suitably secured within the dielectric 8.

It is desirable to use a plurality of spacers or support elements 9 for dielectric 8 and electrode 7. These elements 9 are made of electrically insulating material, and located between the hollow cylindrical dielectric 3 and the second dielectric 8, and hold the second electrode 7, together with the dielectric 8 in mechanically fixed position within the dielectric 3.

The first electrode 5 is sub-divided into a plurality of ring-spaced segments 5', 5" . . . , in order to be able to match the radiating surface to the geometry of the body or body portion to be irradiated. Electrode connections 12', 12", connected to a selector switch, not shown, for example a controllable switch, can connect the electrodes 12', 12" selectively together or separate them; when connected together, a plurality of such ring segments operate as a single electrode 5; only one ring segment, for example ring segment 5' or a selection of ring segments, as determined by the selection via a switch 14 or any similar controllable switch is then connected to a voltage supply source 15 to generate the UV radiation.

The body 3 forms a vessel delimiting the discharge space 4; it is closed at the end facing surfaces in suitable manner—shown only schematically in fragmentary form at 1a—as is well known in the art; it is evacuated before the fill gas is introduced therein. Xenon halide with a cold-fill pressure between about 500 to 1,500 mbar is filled into the discharge space which, then, is hermetically sealed. The fill gas, under discharge conditions, forms excimers.

The first light transmissive electrode 5 is made of a net of VA steel. The two dielectrics 3 and 8 are made of quartz; the hollow cylindrical dielectric vessel 3 is quartz glass, to provide for good transparency for UV radiation; the second, inner electrode 7 is made of an electrically conductive metal rod, preferably tungsten, in order to ensure high temperature. The reflector 2, shown only in schematic and fragmentary representation, is preferably made of aluminum.

The hollow cylindrical dielectric 3 is best seen in FIG. 2; the inner electrode 7 is fitted within the dielectric 8, without any spaces. Portions of the ring segments 5" of the net or mesh electrode 5 likewise can be seen. A switch, shown only schematically at 14, permits, selectively, parallel connection of a plurality of ring segments as partial electrodes of the first electrode 5; the controllable switch 14 is connected to a terminal 16 of the voltage supply source 15. The voltage supply is an a-c supply source.

The second electrode 7 is connected to terminal 13 and through connection 17 with the voltage supply source 15. FIG. 2 also shows that the second electrode 7 is a rod-like element, positioned along the central axis 6 of the outer dielectric 3, and jacketed by the second dielectric 8. The dielectric 8 may be quartz, or quartz glass, respectively.

The discharge space 4 is filled with a fill of xenon chloride. To obtain incoherent excimer radiation in a wavelength of from 300 to 350 nm, a cold-fill pressure in the region of from about 500 to 1,000 mbar is used. To obtain a wavelength of about 308 nm, the xenon chloride fill has a cold-fill pressure of about 750 mbar. To obtain incoherent or non-coherent excimer radiation with a wavelength in the band of from 315 to 350 nm, the discharge space 4 is filled with a xenon chloride fill having a cold-fill pressure between about 750 to 1,500 mbar. The cold fill pressure has an effect on the wavelength of emitted radiation.

To irradiate a body B (FIG. 2), located on a support S, the source 15 is energized; radiation is directed to the body B not only directly, as schematically shown by arrows R, but also from the reflector 2.

Various changes and modifications may be made within the scope of the inventive concept.

The voltage source 15 is controllable with respect to frequency and duty cycle and, for example, may be similar to a voltage source utilized in connection with ozone generators; it should supply power at between about 0.1 and 1 kw (−10 kV) at 300 kHz.

Vessel 3 has an inner diameter of, for example, between about 10–15 mm, preferably about 13 mm, with a wall thickness of about 1–2 mm. Electrode 7 and dielectric 8 have an outer diameter of 3 respectively 5 mm.

We claim:

1. A radiation generating apparatus for generating radiation for application to a human body, for use in optionally generating the radiation in the form of incoherent excimer radiation in a wavelength within the band from about 300 to 315 nm or from about 315 to about 350 nm; comprising a discharge vessel (3) having a confining wall of dielectric material, said wall having an inner surface defining an interior of the vessel and outer surface remote from the interior of the vessel (3);

a first electrode (5) located on said outer surface of the wall of the discharge vessel, said first electrode (5) and said wall of the discharge vessel (3) being radiation transmissive;

a second electrode (7) de-limiting, directly or indirectly, a discharge space (4) within the discharge vessel (3);

a fill of xenon halide having a cold-fill pressure of about from 500 to 1,500 mbar within the discharge space (4) in the discharge vessel (3); and a voltage source (15) connected to said first (5) and said second (7) electrode, for energizing the electrode to cause said apparatus to emit incoherent excimer radiation.

2. The apparatus of claim 1, further including a second dielectric material (8) shielding a surface of the second electrode (7), and facing said first electrode (5).

3. The apparatus of claim 2, wherein said second dielectric material (8) is located on said second electrode (7).

4. The apparatus of claim 1, wherein the discharge vessel (3) is of tubular shape, defining a central axis (6);

said first and second electrodes (5, 7) are coaxially located;

the dielectric wall of the discharge vessel (3) being hollow-cylindrical, and said first electrode (5) surrounding said wall of the dielectric material, and hence the discharge space (4) in form of a ring-shaped jacket; and said second electrode (7) extends along the axis (6) of said tubular discharge vessel, and hence of the ring-shaped jacket of said first electrode;

said tubular vessel being hermetically sealed at opposite facing ends.

5. The apparatus of claim 4, wherein said first electrode (5) comprises at least one ring-shaped segment (5, 5').

6. The apparatus of claim 5, wherein at least two ring-shaped segments (5', 5") are provided forming said first electrode (5); and a controllable switch (14) is provided, selectively connecting a selected one, or several selected ones of said segments (5', 5") to said voltage source (15).

7. The apparatus of claim 4, wherein said first electrode comprises a metal net or mesh structure.

8. The apparatus of claim 7, wherein said first electrode (5) comprises at least one ring-shaped segment (5, 5').

9. The apparatus of claim 1, wherein said xenon halide comprises xenon chloride having a cold-fill pressure in the discharge space (4) of between about 500 to 1,000 mbar to generate incoherent excimer radiation in the wavelength range of between about 300 to 315 nm.

10. The apparatus of claim 9, wherein, to generate excimer radiation in a wavelength of about 308 nm, the xenon chloride within said discharge space (4) has a cold-fill pressure of about 750 mbar.

11. The apparatus of claim 1, wherein said xenon halide comprises xenon chloride having a cold-fill pressure in the discharge space (4) of between about 750 to 1,500 mbar to generate incoherent excimer radiation in the wavelength range of between about 315 to 350 nm.

12. The apparatus of claim 1, further including a reflector (2) optionally of aluminum, for directing said radiation to a human body (B), or a portion thereof, for phototherapy, or tanning.

13. A device for phototherapy, or tanning of the human body, comprising the apparatus as claimed in claim 1 and further comprising means (S) for positioning the human body (B), or a portion thereof, to be exposed to the radiation (R) emitted from said apparatus as defined in claim 1.

14. The device of claim 13, further including reflector means (2), optionally of aluminum, for directing the radiation emitted by said apparatus, as defined in claim 1, towards the human body.

* * * * *